(12) United States Patent  (10) Patent No.: US 7,647,928 B2
Muellinger et al.  (45) Date of Patent: Jan. 19, 2010

(54) INHALATION DEVICE AND INHALATION DEVICE COMPONENT

(75) Inventors: Bernhard Muellinger, Munich (DE);
Axel Fischer, Moischeid (DE);
Dorothee Koerber, Augsburg (DE);
Andreas Wenker, Landsberg am Lech (DE); Tobias Kolb, Munich (DE);
Sascha Roeder, Munich (DE); Gerhard Scheuch, Wohratal (DE)

(73) Assignee: Activaero GmbH, Germunden (DE)

( * ) Notice: Subject to any disclaimer, the term of this patent is extended or adjusted under 35 U.S.C. 154(b) by 689 days.

(21) Appl. No.: 11/358,263

(22) Filed: Feb. 21, 2006

(65) Prior Publication Data

US 2006/0191537 A1  Aug. 31, 2006

(30) Foreign Application Priority Data

Feb. 23, 2005 (EP) ................................. 05003882

(51) Int. Cl.
*A61M 11/00* (2006.01)

(52) U.S. Cl. .............................. 128/206.22; 128/206.29

(58) Field of Classification Search ............ 128/200.11, 128/200.12, 200.13, 206.22, 206.29, 206.28
See application file for complete search history.

(56) References Cited

U.S. PATENT DOCUMENTS

| | | | |
|---|---|---|---|
| 1,395,948 A | 11/1921 | Drager | |
| 3,490,452 A | 1/1970 | Greenfield | |
| 3,874,379 A | 4/1975 | Enfield et al. | |
| 4,573,463 A | 3/1986 | Hall et al. | |
| 4,807,617 A | 2/1989 | Nesti | |
| 4,890,609 A | 1/1990 | Wilson, II et al. | |
| 4,991,576 A | 2/1991 | Henkin et al. | |
| 5,020,530 A | 6/1991 | Miller | |
| 5,253,641 A | 10/1993 | Choate et al. | |
| 5,727,542 A | 3/1998 | King | |
| 5,871,011 A | 2/1999 | Howell et al. | |
| 5,957,128 A * | 9/1999 | Hecker et al. | 128/204.22 |
| 6,076,524 A | 6/2000 | Corn | |
| 6,089,225 A * | 7/2000 | Brown et al. | 128/200.29 |
| 6,135,109 A | 10/2000 | Blasdell et al. | |
| 6,354,291 B1 * | 3/2002 | Brown et al. | 128/200.29 |
| 6,631,721 B1 | 10/2003 | Salter et al. | |
| 6,758,212 B2 * | 7/2004 | Swann | 128/201.25 |
| 7,481,219 B2 * | 1/2009 | Lewis et al. | 128/206.11 |
| 2002/0017296 A1 | 2/2002 | Hickle | |
| 2003/0168062 A1 * | 9/2003 | Blythe et al. | 128/203.12 |
| 2005/0028811 A1 * | 2/2005 | Nelson et al. | 128/200.11 |

FOREIGN PATENT DOCUMENTS

EP  06003113  6/2006

OTHER PUBLICATIONS

European Search Report, dated Jun. 9, 2006 (5 pages).
European Search Report for EP Application No. 06003113.5, mailed Aug. 2, 2006 (11 Pages).
European Search Report, issued Jun. 14, 2005 (4 pages).

* cited by examiner

*Primary Examiner*—Steven O Douglas
(74) *Attorney, Agent, or Firm*—Faegre & Benson LLP

(57) ABSTRACT

The invention relates to a component for an inhalation device comprising a first flow channel for inhalation, a second flow channel for exhalation, a mouthpiece forming a part of the first flow channel, a filter assigned to the second flow channel and a protection element which circumferentially surrounds the mouthpiece and is sealingly connected the mouthpiece at the end opposing the tip of the mouthpiece.

22 Claims, 16 Drawing Sheets

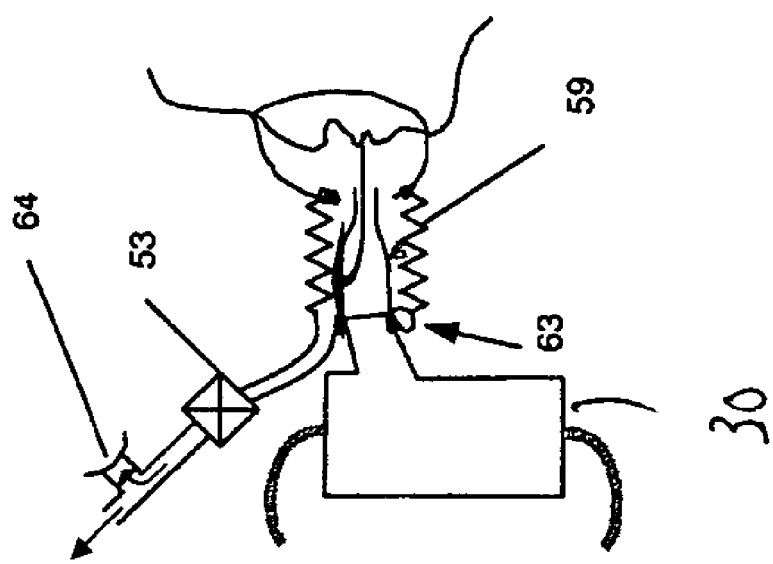

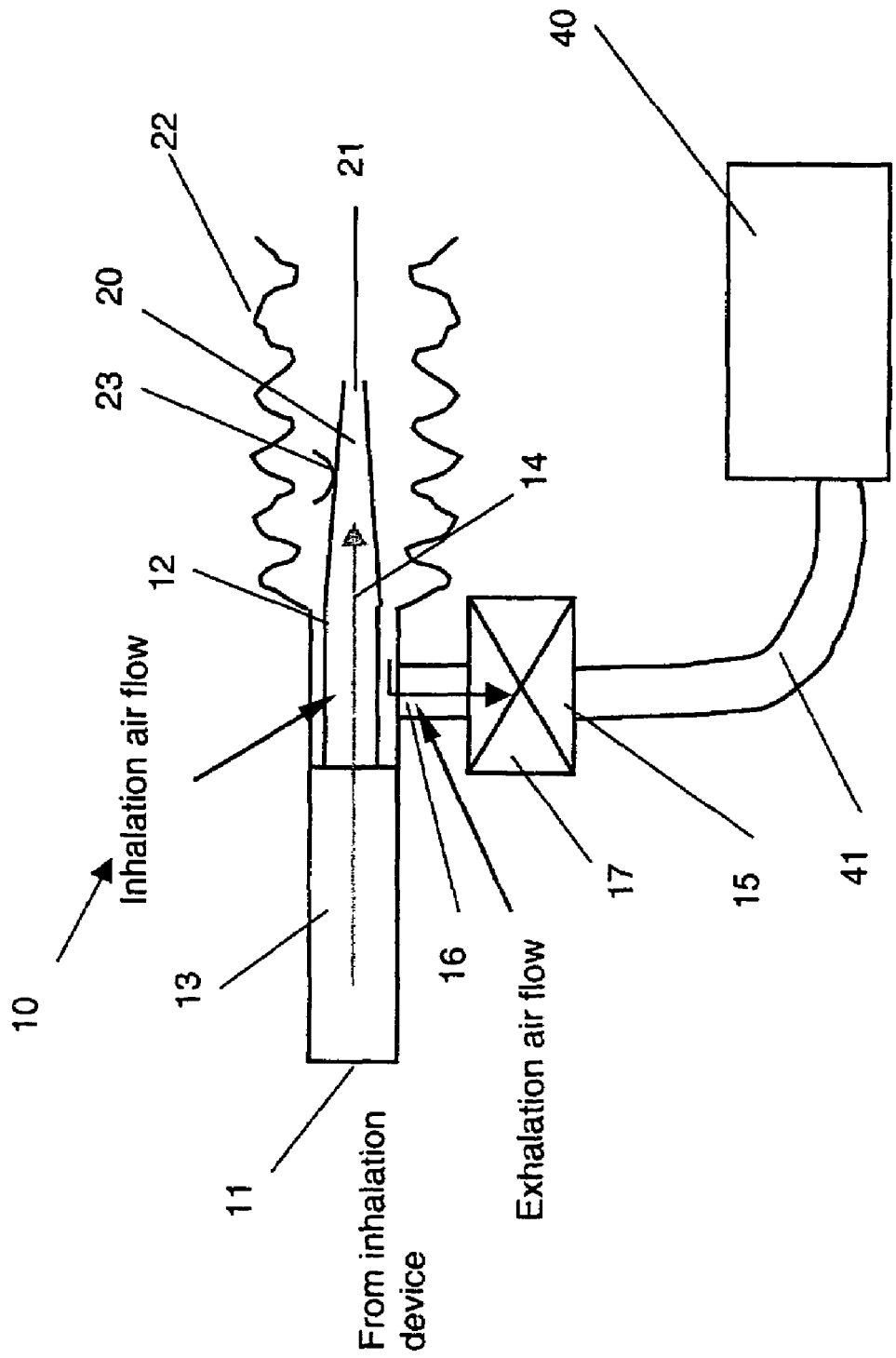

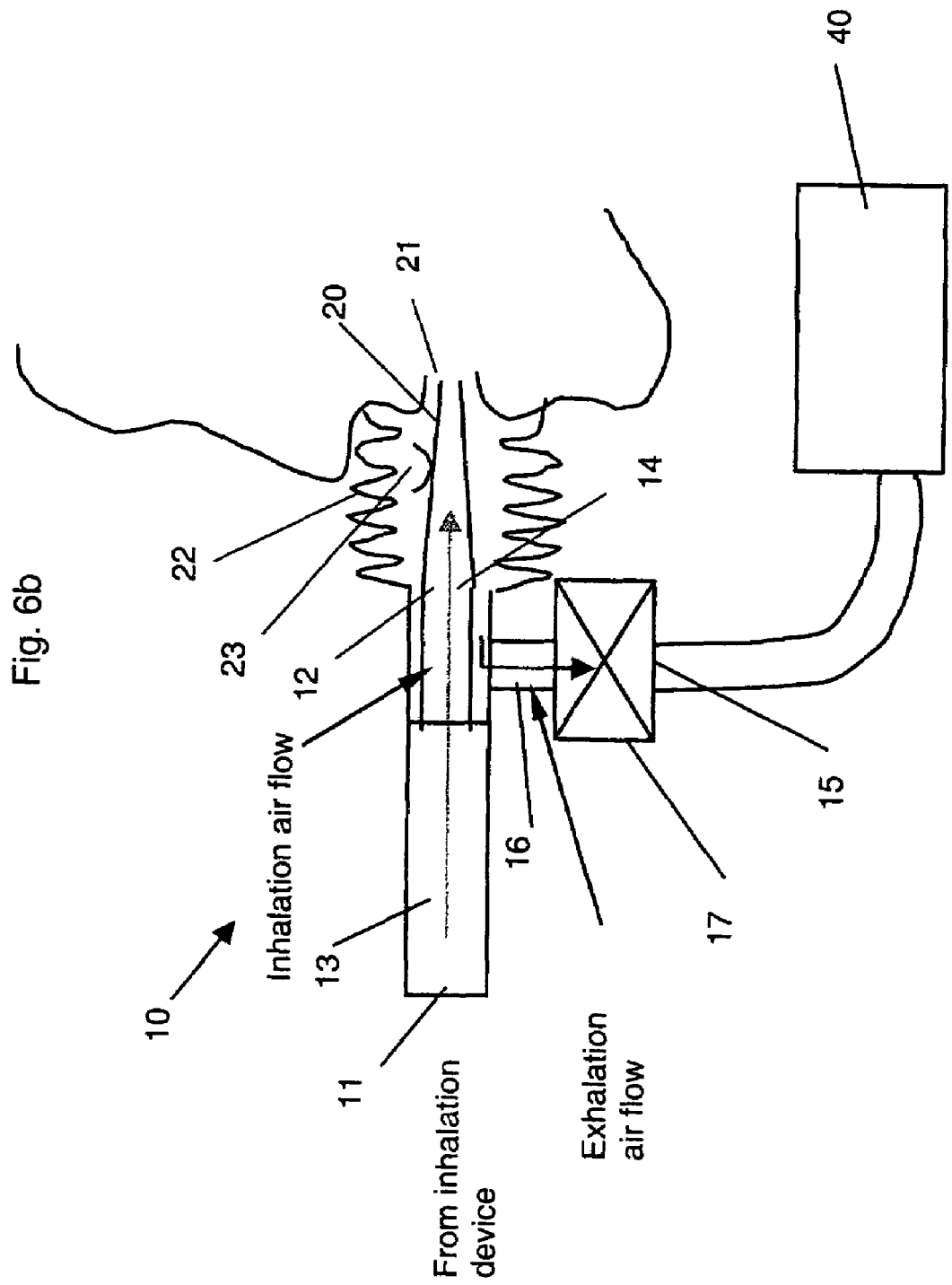

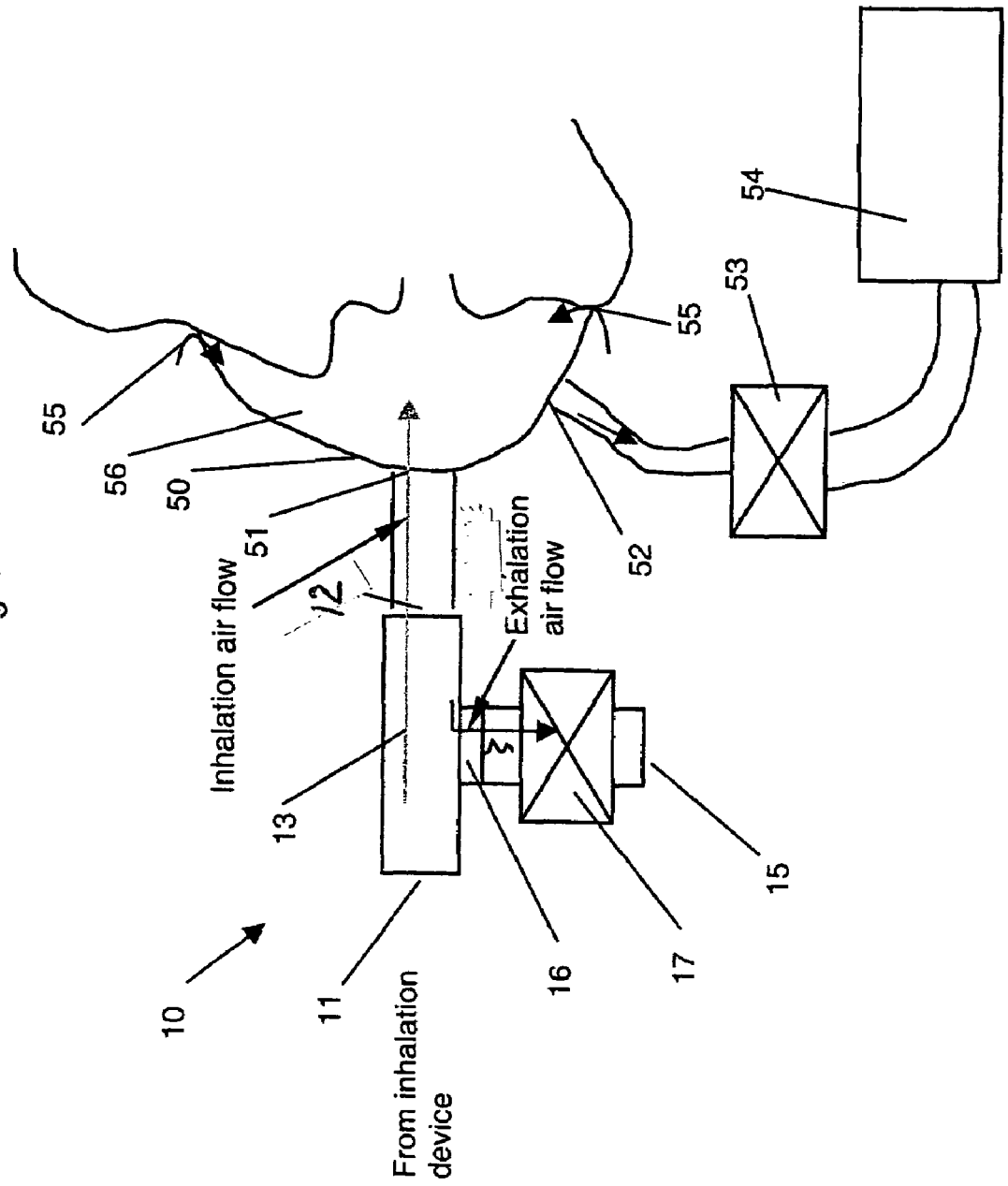

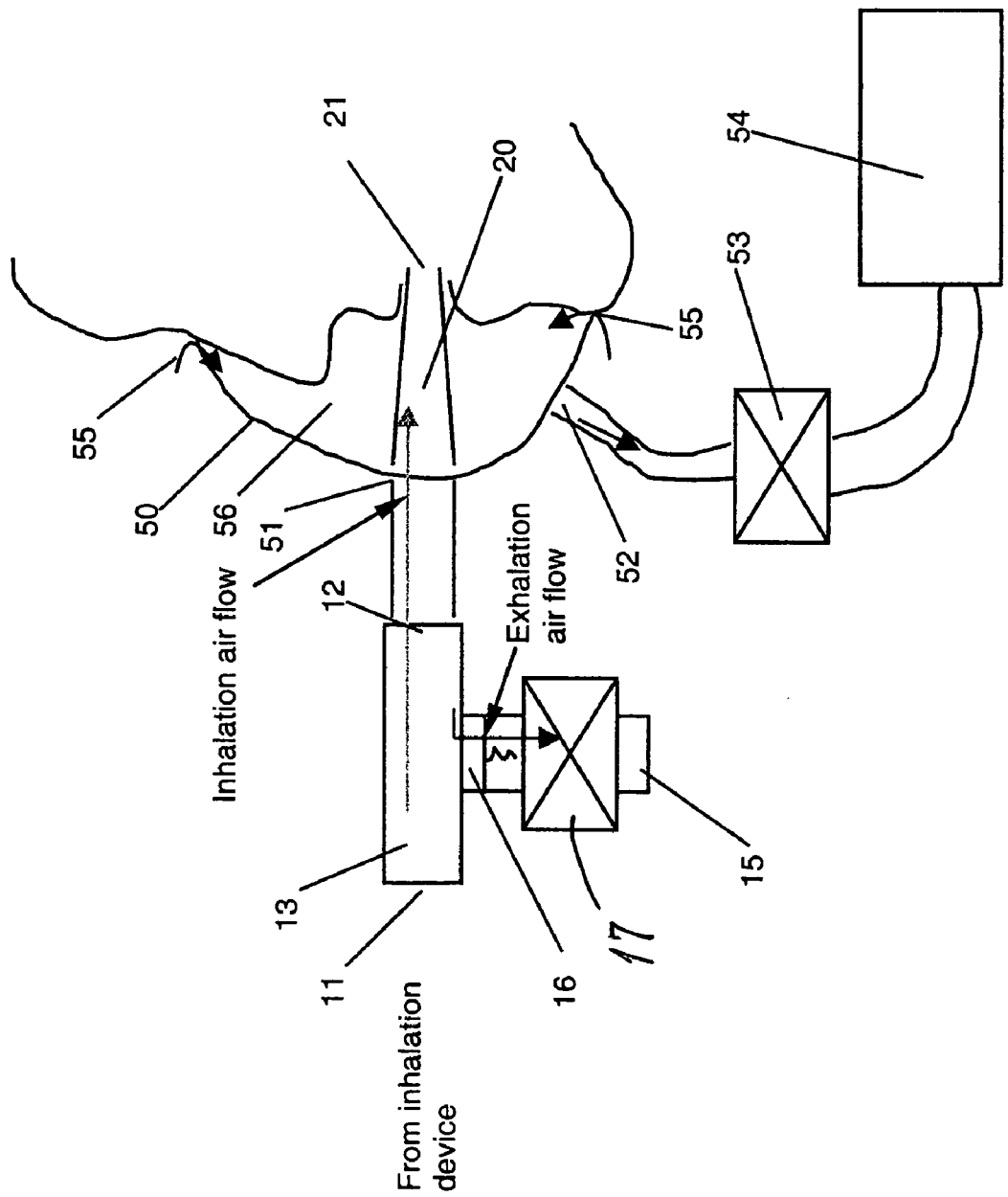

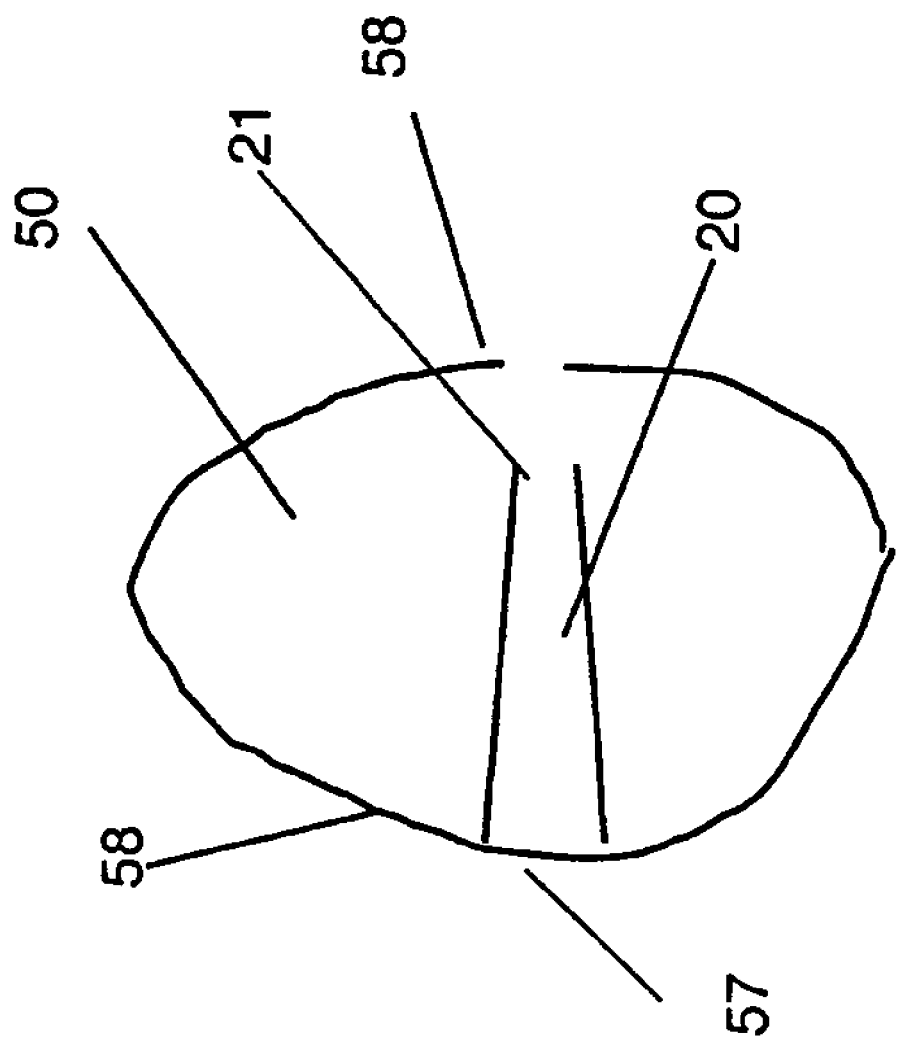

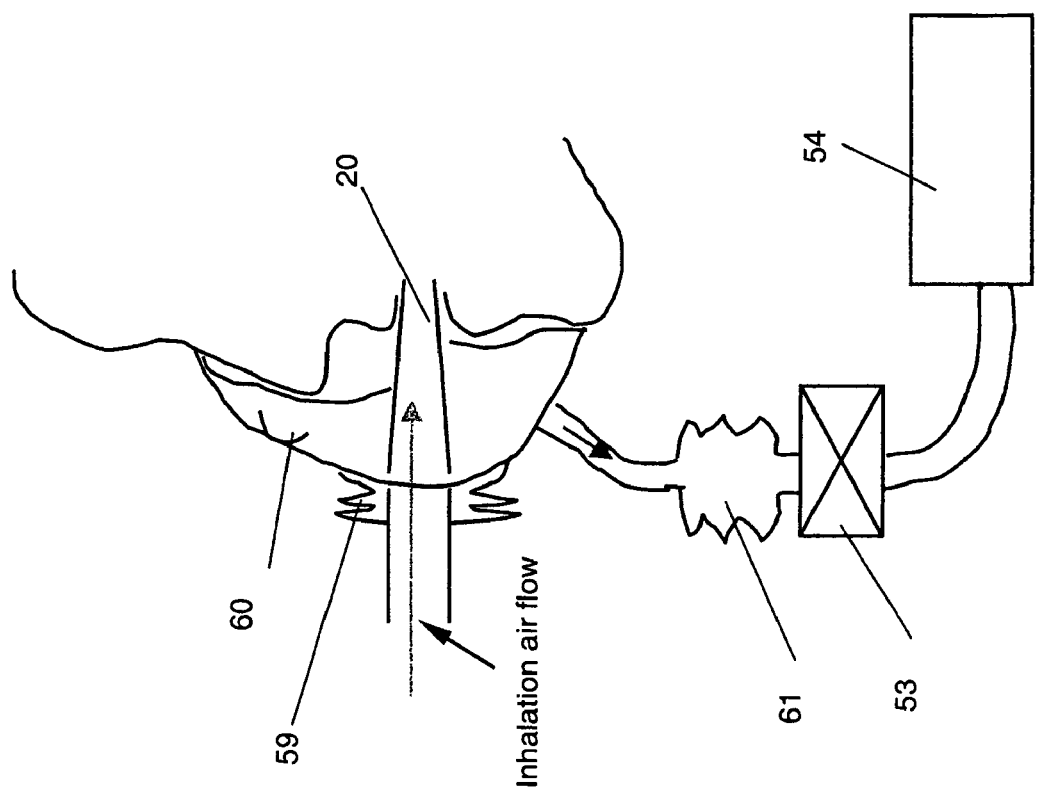

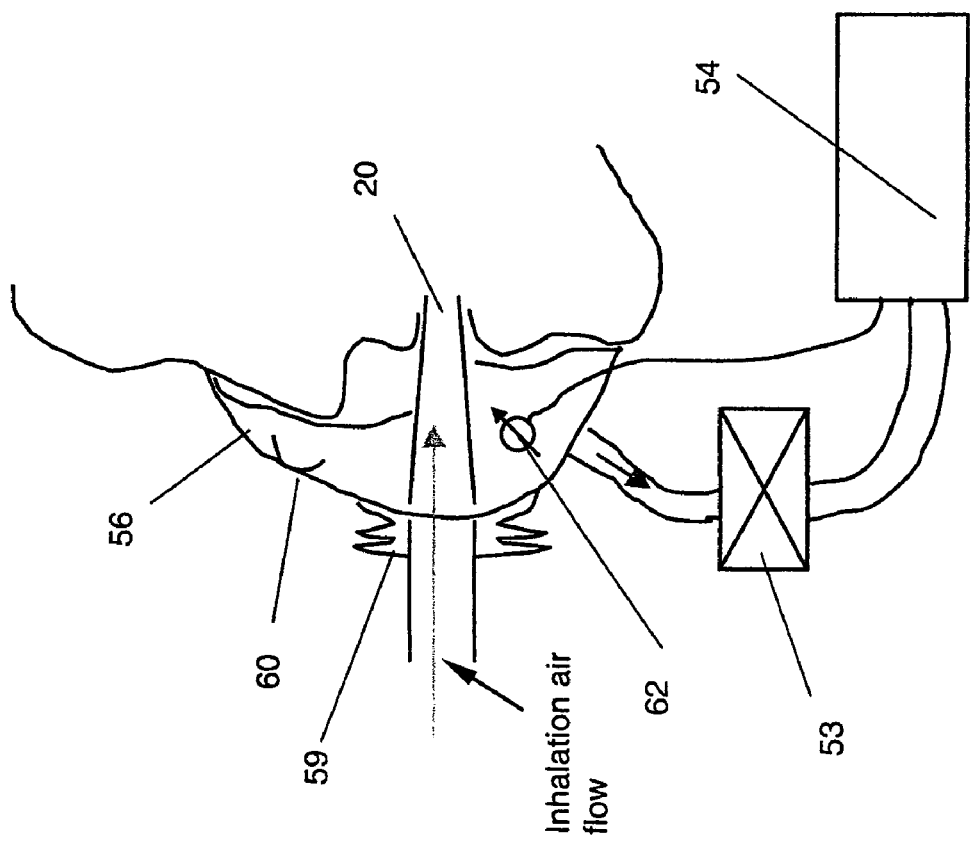

INHALATION DEVICE AND INHALATION DEVICE COMPONENT

REFERENCE TO RELATED APPLICATION

This application claims priority to European Patent Application 05 00 3882.7 filed Feb. 23, 2005.

The present invention relates to a component for an inhalation device and, in particular, to an inhalation device for inhalation of toxic active ingredients.

BACKGROUND

U.S. Pat. No. 5,871,001 relates to an apparatus for delivery of anaesthetic gas to a patient. Said apparatus has a mask which overlies the patient's face around the mouth and face but which does not abut against the face. Supplied gas is conveyed to the mouth of the patient via a flow channel and a mouthpiece. A flow channel is also provided for exhalation. When the patient exhales, the exhalate flows into the exhalation flow channel via a valve. If the patient does not exhale through the mouthpiece but, e.g., through the nose into the interior of the mask, said exhalate also flows into the flow channel for exhalation.

Inhalation is a way which is getting more and more important for the administration of pharmaceuticals. To this end, apart from the use of new locally acting pharmaceuticals for the therapy of lung diseases, new therapeutic strategies are developed making use of the lung as aditus for systematically acting substances.

Possibly, toxic active ingredients have to be applied by inhalation. For instance, cytostatic drugs (e.g., cisplatinum) or cytocines may be administered to a patient with lung cancer. When toxic active ingredients are administered, it must always be ensured that the contamination danger of the environment or possibly present persons with these toxic active ingredients is ruled out or kept as low as possible. For instance, residues of the toxic active ingredients can be exhaled from the patient's lung during the exhalation process. These circumstances are not taken sufficiently into account by conventional inhalation apparatuses or said apparatuses are very uncomfortable.

SUMMARY OF THE INVENTION

It is the object of the invention to enable the inhalation of toxic active ingredients by eliminating or reducing potential risks or a contamination of the environment of the patient treated. This object is achieved with a component for an inhalation device as well as with an inhalation device according to the claims.

According to a first embodiment, the present invention relates to a component for an inhalation device. The component according to the invention comprises a first flow channel for inhalation and a second flow channel for exhalation. Furthermore, the component has a mouthpiece, which forms a part of the first flow channel, a filter assigned to the second flow channel and a protection element surrounding the mouthpiece in circumferential direction. The protection element is sealingly connected to the mouthpiece at the end opposing the tip of the mouthpiece.

The component may further comprises an inhalation mask, which is connected to the end of the protection element opposing the junction between mouthpiece and protection element. The flow channel for exhalation preferably starts at the junction between mouthpiece and protection element. Alternatively, the flow channel for exhalation starts at the inhalation mask.

According to another embodiment, the second flow channel is connectable to a suction device. The second flow channel for exhalation may also comprise an expiration valve. The expiration valve is located downstream from the filter.

In a further embodiment, the wall of the mouthpiece comprises an expiration valve.

The first flow channel for inhalation is connectable to a nebulizer.

The excess length of the protection element, e.g., of a mask with regard to the tip of the mouthpiece, is preferably between 5 and 100 mm. The protection element is preferably self-expandable and is formed, e.g., as bellows.

According to a second embodiment, the present invention relates to a component for an inhalation device. The component according to the invention comprises a first flow channel for inhalation extending between a first air inlet opening and a first air outlet opening. Further, a second flow channel for exhalation is provided which extends between a second air inlet opening and a second air outlet opening. The first air outlet opening and the second air inlet opening coincide so that one and the same opening serves as air outlet opening for the first flow channel and as air inlet opening for the second flow channel. Alternatively, the first air inlet opening and the first air outlet opening as well as the second air inlet opening and the second air outlet opening coincide so that there are only a first and a second opening which form the two flow channels.

The component according to the invention further comprises a filter which is arranged in the second flow channel, i.e., it is assigned to the second flow channel/the second opening, and is provided, e.g., in extension of the second flow channel, i.e., downstream. The second flow channel may be then opened and the first flow channel is closed when the inhalation by the patient is terminated, be it via abortion or after time lapse at the end of the necessary inhalation time or at the end of one's breath.

Moreover, the component comprises an inhalation mask in which the first flow channel ends and at which the second flow channel begins. The inhalation mask further comprises a third air inlet opening in the form of a valve for a third flow channel. The third flow channel ensures a continuous air flow and prevents the mask from being pressed too strongly against the face due to the suction. According to the invention, exhalation takes place via the second flow channel.

When the component according to the invention is used in an inhalation device, the patient may inhale through the first flow channel. To this end, the first air inlet opening is connectable upstream to a nebulizer, which introduces the active ingredient to be applied, e.g., in the form of aerosol, in a compressed air flow. The patient inhales via a mouthpiece which is connected to the first air outlet opening downstream from the first flow channel. Exhalation takes place in the opposite direction via the mouthpiece by means of an exhalation valve, however, afterwards not via the first flow channel back towards the nebulizer but instead via the second flow channel to the filter, which filters out the residues of the toxic agent present in the exhaled air. It may also be exhaled in the mask by removal of the mouthpiece.

A suction device may be attached downstream to the filter. This is advantageous in that upon termination of the inhalation, not only the exhaled air of the patient is filtered but also the second flow channel and the mouthpiece are actively sucked out and thus emptied so that no toxic agents can reach the environment from the mouthpiece opening after removal of the mouthpiece. An exhalation buffer may be provided in said suction channel, which buffers the exhaled air if the suction rates are too low. The exhalation buffer is then further emptied, e.g., during the next inhalation step. The suction flow is preferably between 15 and 80 l/min.

The first flow channel and the second flow channel may form a three-way valve. The three openings correspond to (i) the first air inlet, (ii) the first air outlet/second air inlet and (iii) the second air outlet. Alternatively, two separate flow channels are provided, wherein, e.g., a one-way valve is provided at the first air outlet opening, which only permits inhalation, i.e., an air flow to the patient, and a one-way valve is also provided at the second air inlet opening, which permits only exhalation. Thus, it is ensured that exhalation takes place only via the second flow channel.

In another embodiment, a protection element is provided downstream from the first air outlet opening and/or the second air inlet opening, which is preferably self-expandable, e.g., bellows. The protection element surrounds the first air outlet opening and/or the second air inlet opening and, where required, a mouthpiece. The protection element is sealingly connected to, e.g., the end of the mouthpiece which is opposite the tip of the mouthpiece. In its idle state, the protection element is expanded but may be compressed upon use of the inhalation device. In its expanded state, the protection element extends beyond the tip of the mouthpiece like a receptacle. Consequently, when the user removes the inhalation device from the mouth, the protection element expands automatically in order to thus provide its protective function: the contaminated air is being kept in the protection element and cannot escape into the environment, but is sucked out and filtered. The protection element may have an exhalation valve in order to enable the patient to exhale or exhale more easily before the inhalation process starts or during a break. Thus, the user may exhale into the interior of the protection element and air escapes via the exhalation valve. In one embodiment the protection element extends over the entire component according to the invention (similarly to a balloon) so that all possible leakages are covered and no contaminated air can escape into the environment but is blocked by the protection element.

The excessive length of the protection element is preferably between 5 and 100 mm. The suction flow is preferably between 15 and 80 l/min. The greater the excessive length, the smaller the suction flow, wherein there is no emission of aerosol yet.

The inhalation mask of the component according to the first and second aspects of the invention is designed and dimensioned preferably such that it may cover the user's mouth and nose so that the air exhaled via the mouth or nose gets into the interior of the mask. For example, this is a CPAP (Continuous Positive Airway Pressure) mask known from ventilation. According to a first alternative, the inhalation mask has an opening where, e.g., a tube connection ends between the flow channels and the inhalation mask (the flow channels may also directly lead into the interior of the mask). The inhalation mask may be flush with the tube connection so that the inhalation mask extends the tube connection like a funnel-shaped element. In this alternative, a mouthpiece, which a patient puts into the mouth, is not compulsorily provided. As an alternative a mouthpiece is provided and penetrates the inhalation mask and projects into the interior of the mask formed between the inhalation mask and the face of the user. The mouthpiece projects thus far into the inhalation mask that the user can easily put the end or the tip of the mouthpiece into the mouth to inhale/exhale. In this embodiment, the design may be such that the mouthpiece is movable relative to the inhalation mask. The mouthpiece may be movable between a first position (the inhalation state) in which the user can put the mouthpiece into the mouth and a second position (exhalation state) in which the mouthpiece is withdrawn in the interior of the mask. This is advantageous in that the user can put the mouthpiece into the mouth for inhalation but releases and withdraws it for exhalation so that the exhalation is not carried out towards the nebulizer but the interior of the mask. Furthermore, the user can thus breath in air from time to time without inhaling or without having to remove the mask.

In another embodiment, a flexible element is provided as link between the mouthpiece and the mask. More preferably, the flexible element is self-expanding so that the mouthpiece after being released by the patient, is automatically withdrawn by the expansion of the flexible element.

According to another embodiment, the inhalation mask of the component according to the first or second embodiment is designed such in the circumferential area that a pressure compensation can take place via the circumferential area of the inhalation mask in case of a negative pressure in the interior of the mask. This means that the circumferential area of the inhalation mask is designed such that it does not abut the patient's skin absolutely tightly but permits the flow of air into the interior of the mask if there is a negative pressure. This is particularly advantageous when a suction device sucks out the air in the inhalation mask interior via a corresponding opening since then the suction device may be continuously operated, e.g., as a safety measure, and in case of a negative pressure, ambient air flows into the interior of the mask for pressure compensation. However, exhalation air contaminated with the toxic agent cannot escape via the circumferential area of the inhalation mask since the suction device is responsible for sucking it out.

As an alternative to the possibility of admitting an air flow via the mask edge, the mask has one-way valves ensuring the necessary pressure compensation. The valves may be provided in the front part of the mask, i.e., away from the mouth of the user.

The inhalation mask may be designed in the form of a balloon. Preferably, the mouthpiece penetrates the balloon-like inhalation mask in a first portion, turned away from the user's face, and extends into the interior of the mask. A second portion opposing this portion, turned towards the user's face during inhalation, is closed prior to the inhalation and is only penetrated by the tip of the mouthpiece at the beginning of the inhalation in that the user attaches this mask portion to his/her face and moves the mouthpiece end in the interior of the inhalation mask to the mouth.

The component according to the invention may be a part of the aerosol generator of the inhalation device.

A third embodiment of the invention relates to an inhalation device comprising a first flow channel for inhalation and a second flow channel for exhalation, wherein means are provided which prevent active ingredients from escaping into the environment before or prior to, during or after inhalation by the user using the inhalation device.

According to an alternative the third embodiment of the present invention, an inhalation device is provided comprising a component of the invention according to the first embodiment as well as a nebulizer which is connected to the first air inlet opening and a mouthpiece which is connected to the first air outlet opening and the second air inlet opening. The inhalation device may comprise a suction device which is connected to the second air outlet opening of the component such that exhaled air is sucked out via the filter of the component.

Alternatively, the inhibition means may comprise an inhalation mask with a first opening for inhalation and a suction opening, and further with a nebulizer connected to the first opening and a suction device connected to the suction opening.

The inhalation device according to the invention only triggers the nebulization of the active ingredient if the patient or the user creates a slight negative pressure at the mouthpiece and thus signalling the wish to inhale. The nebulization preferably terminates immediately when the negative pressure at the mouthpiece ceases.

The suction of the exhaled air of the user is preferably started only when the nebulizer creates aerosol at all since only then there is the danger that toxic agents are exhaled into the environment. This means that the suction does not start before the user/patient begins to inhale since this triggers the nebulization. When the patient stops during the inhalation, the suction continues, and the suction is preferably increased to empty the flow channels immediately. Upon a normal termination of the inhalation, the nebulization of the active ingredient stops but the suction continues when the exhalation starts. Even after the user has exhaled, the suction is maintained for a certain period of time to suck out potential residues of contaminated exhaled air.

BRIEF DESCRIPTION OF THE DRAWINGS

The invention is hereinafter explained in further detail with the drawings.

FIG. 1b illustrates the component of FIG. 1a during exhalation.

FIG. 6a illustrates a component according to a second embodiment of the invention.

FIG. 6b illustrates the use of the component of FIG. 6a by a patient.

FIG. 7 illustrates a component according to a third embodiment of the invention.

FIG. 8 illustrates a component according to a fourth embodiment of the invention.

FIG. 12 illustrates a schematic depiction of an inhalation mask.

FIG. 13 illustrates a further alternative embodiment of the inhalation mask.

FIG. 14 illustrates a further alternative embodiment of the inhalation mask.

FIGS. 1a and 1b illustrated a first embodiment of a component according to the invention. A mouthpiece 20, which the patient can put in his/her mouth for inhalation, is connected to a nebulizer 30. This is a first flow channel 13 for the inhalation. The mouthpiece 20 is surrounded by a flexible protection element 59, which is preferably self-expandable, e.g., bellows. The protection element 59 is expanded in its idle state, as shown for example in FIGS. 1b and 3; however, it is compressible upon use of the inhalation device, as is shown in FIGS. 1a and 2. In its expanded state, the protection element 59 preferably extends beyond the tip 21 of the mouthpiece 20. Thus, when the user removes the inhalation device, i.e., the mouthpiece 20, from the mouth, the protection element 59 expands automatically in order to thus provide its protective function: contaminated air is being kept in the protection element 59 and cannot escape into the environment, but is sucked off and filtered, as will be described further below.

Figure 1A:
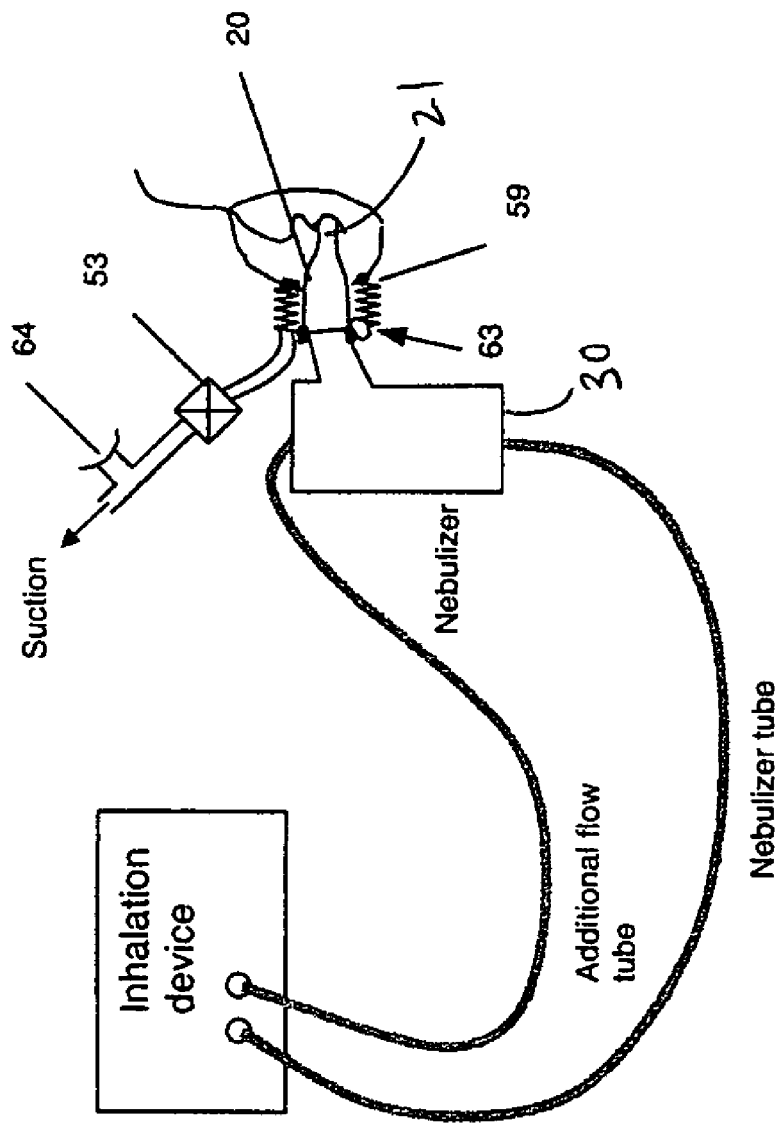
FIG. 1a illustrates a component according to a first inventive embodiment during inhalation.

The component illustrated in FIGS. 1a, 1b and 2 to 4 further comprises an exhalation path 65, which is a second flow channel 16 for exhalation. The exhalation path 65 is preferably situated at the junction 66 between the mouthpiece 20 and the flexible element 59, as can be clearly seen in FIGS. 2 and 3. In order to ensure that the user can exhale or exhale more easily prior to the inhalation process or during an inhalation break (FIG. 3), the exhalation path 65 preferably comprises an exhalation or expiration valve 64. A suction device 54 is preferably connected to the exhalation path 65, wherein said device sucks off via an exhalation filter 53 the contaminated air exhaled by the patient. The expiration valve 64 is advantageous in that the patient can exhale in a stronger flow than the suction device 54 sucks off. Moreover, upon failure of the suction device 54, the patient may convey, by continuous breathing, the contaminated air from the system into the filter 53. This means that exhalation is performed via the filter 53 and then either via the suction 54 and/or the expiration valve 64.

In the embodiment according to FIGS. 1a to 4, a mask 50 is attached to the end of the flexible element 59 facing the patient, wherein the mask covers the mouth and nose of the patient so that contaminated air may only flow in or out of the interior of the flexible element 59 and thus to the expiration filter 53. As illustrated in phantom in FIG. 2, the exhalation path 65' can also alternatively begin at the mask 50, i.e., it may be opened directly towards the interior of the mask and not to the bellows 59.

As described, the exhalation path 65 starts preferably at the junction 66 between mouthpiece 20 and flexible element 59. In the embodiment according to FIGS. 2 and 3, an inspiration valve 63 is optionally arranged in this area. This allows a pressure compensation during exhalation as well as an inspiration prior to the beginning of the inhalation process or during inhalation breaks.

Figure 2:
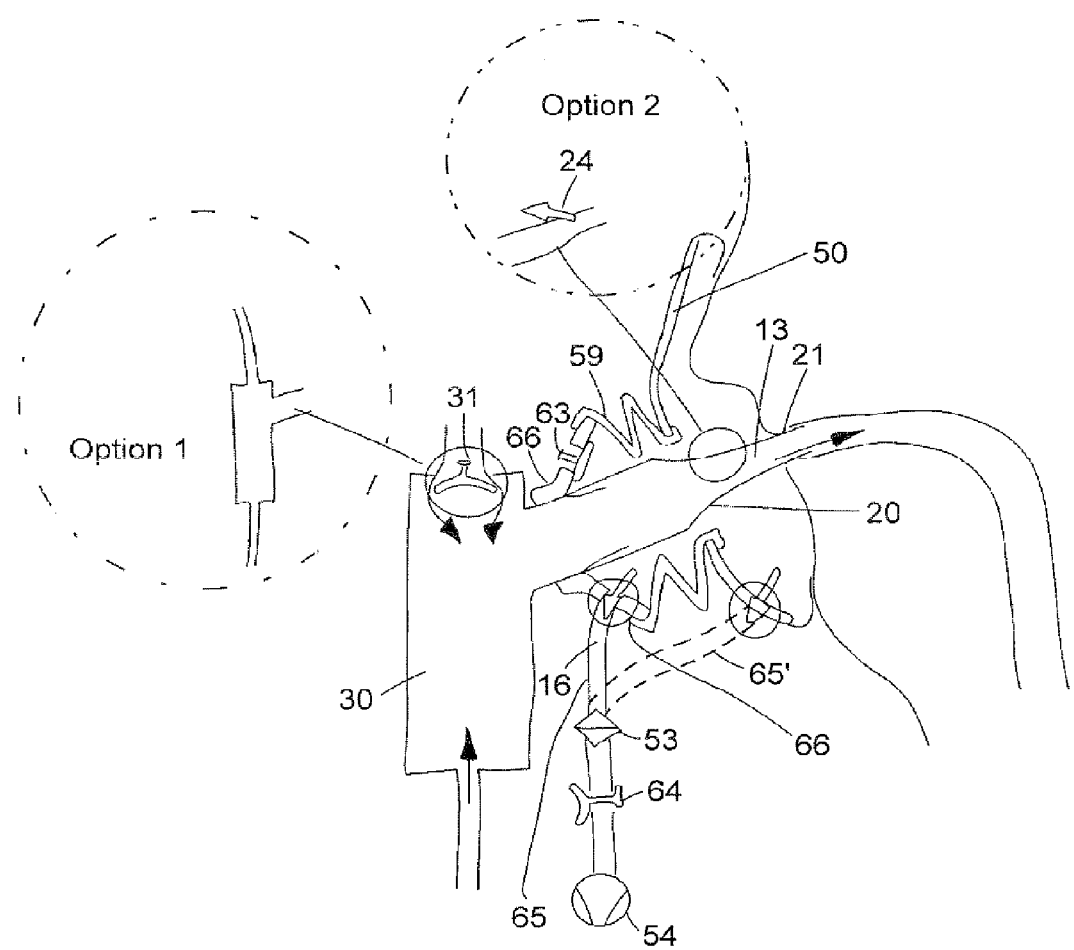
FIG. 2 illustrates a detailed depiction of the component of FIG. 1 together with optional features.

As a further option illustrated as Option 2 in FIG. 2, the mouthpiece 20 itself has a valve 24. This is advantageous in that the patient does not necessarily have to put the mouthpiece 20 out of the mouth during exhalation. An exhalation against the resistance of the nebulizer 30 leads to an opening of the mouthpiece valve 24 so that the contaminated air then reaches the interior of the mask 50 and the bellows 59 and can be sucked off.

The nebulizer 30 connected to the mouthpiece 20 can either be a nebulizer to which the aerosol is fed by an inhalation pump, while additional air is fed via a corresponding valve 31, or it can be a nebulizer with controlled additional air, like the nebulizer of the AKITA system of Activaero GmbH. The latter is shown as Option 1 in FIG. 2.

Figure 3:
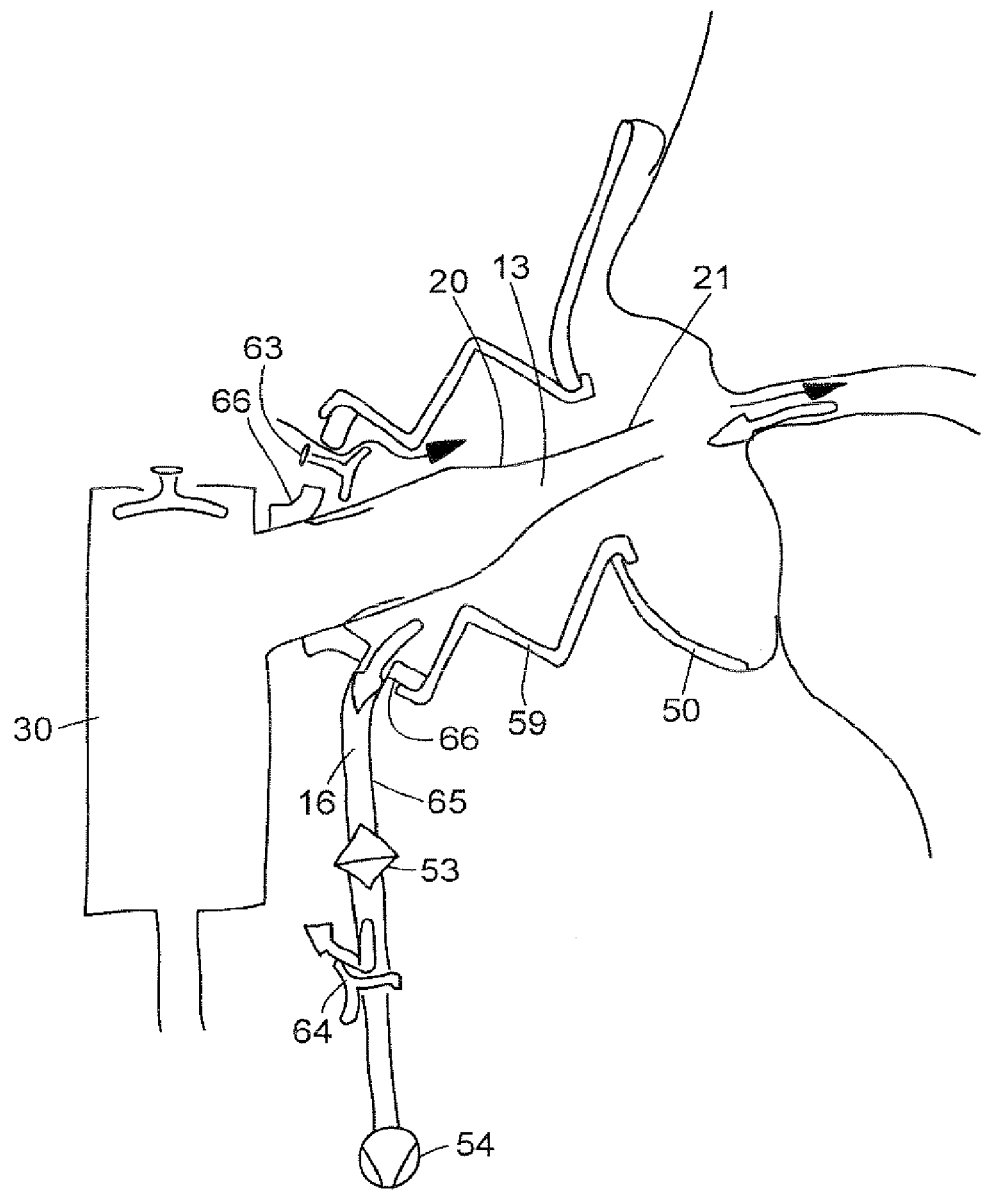
FIG. 3 illustrates the component of FIG. 2 during the inhalation break.

The respective air flows are shown in FIGS. 2 and 3 with thin arrows (aerosol, inspiration) and thick arrows (exhalate, expiration).

Figure 4:
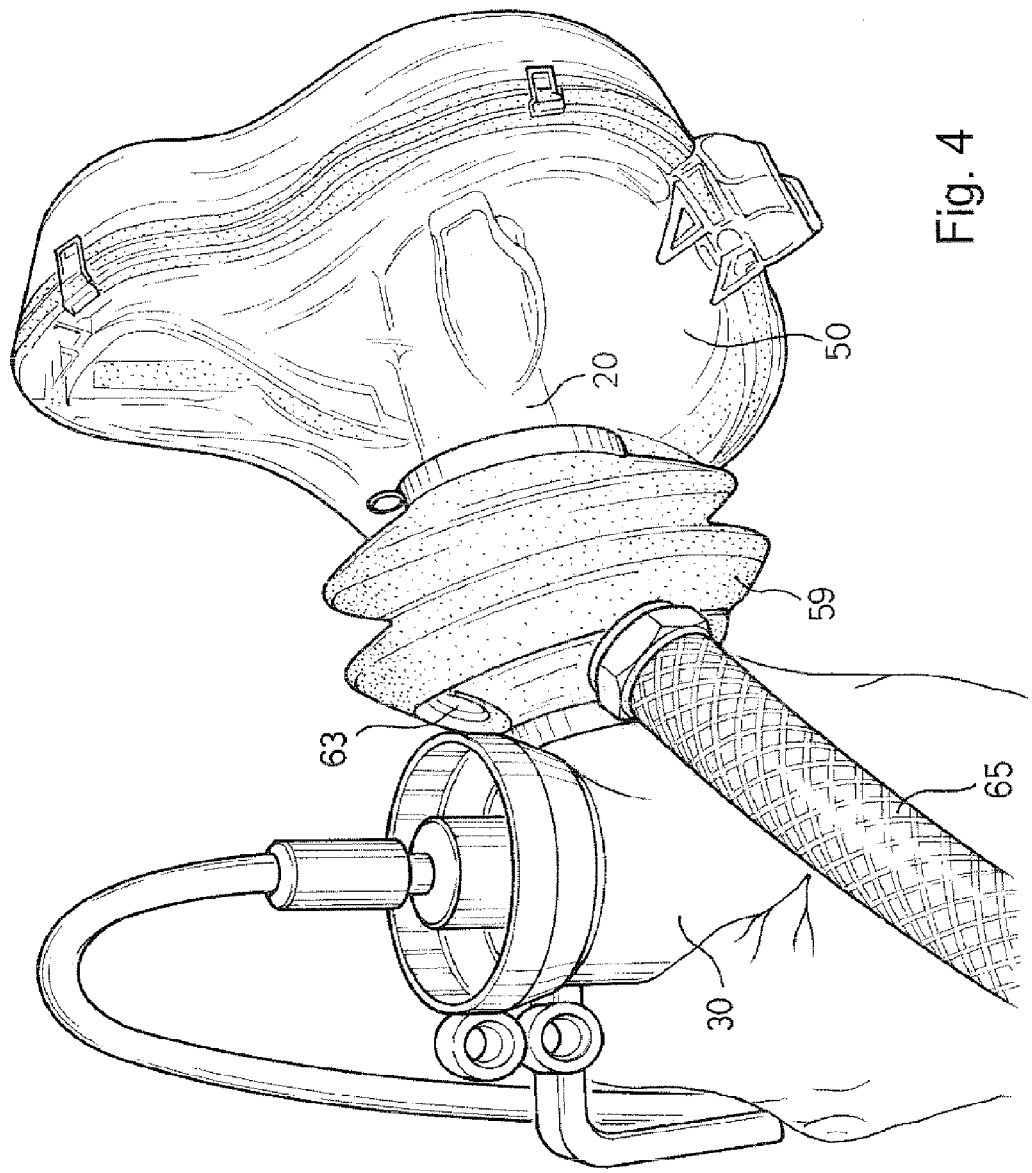
FIG. 4 illustrates a perspective view of a practical example of the component of FIG. 2.

FIG. 4 is an example of the component of the invention according to FIGS. 2 and 3. FIG. 4 clearly shows the bellows 59 attached to the nebulizer together with the mask 50 and mouthpiece 20 as well as the exhalation tube 65, which leads to the suction device.

Figure 5:
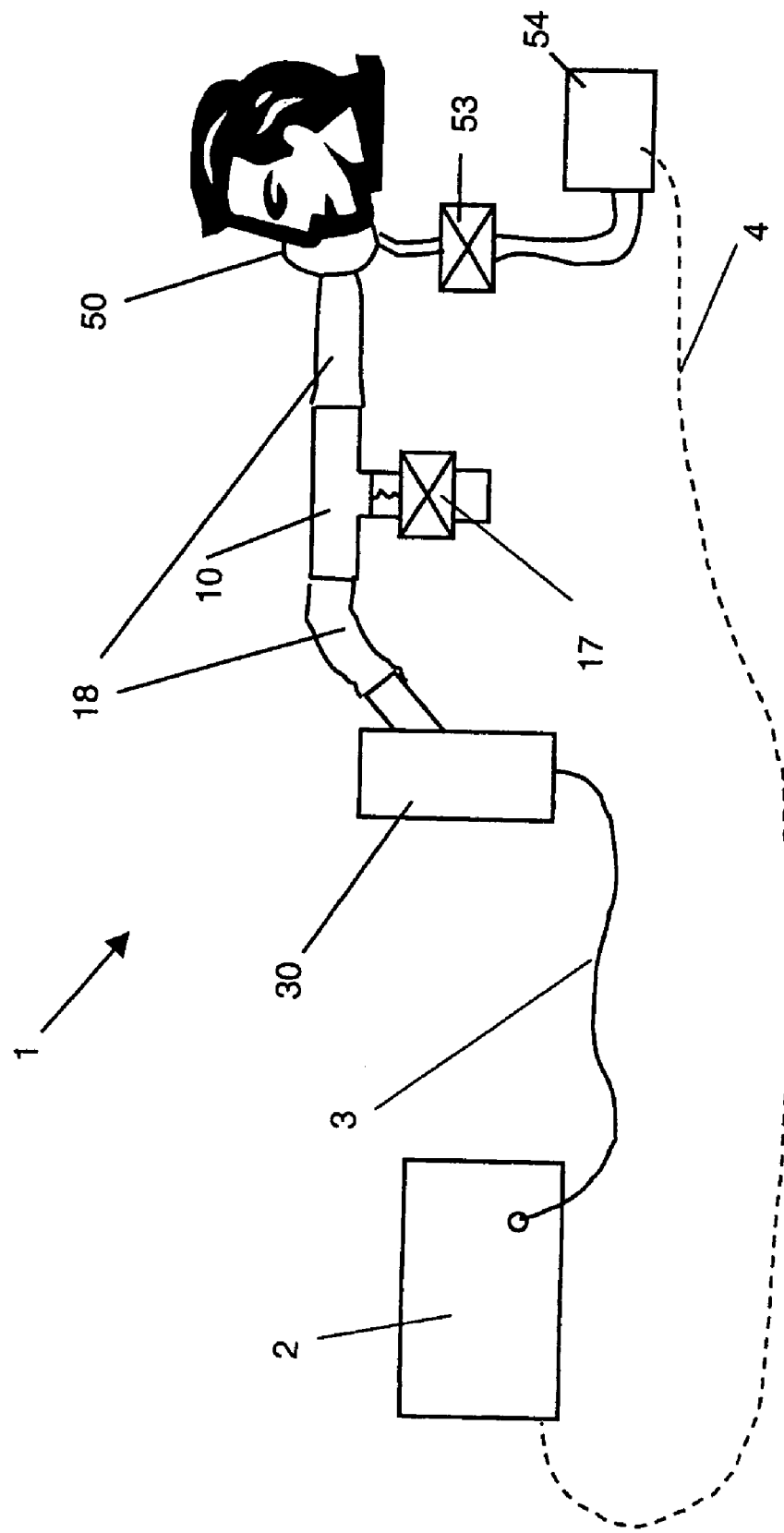
FIG. 5 illustrates the basic structure of an inhalation device for the inhalation of toxic pharmaceuticals.
Figure 9:
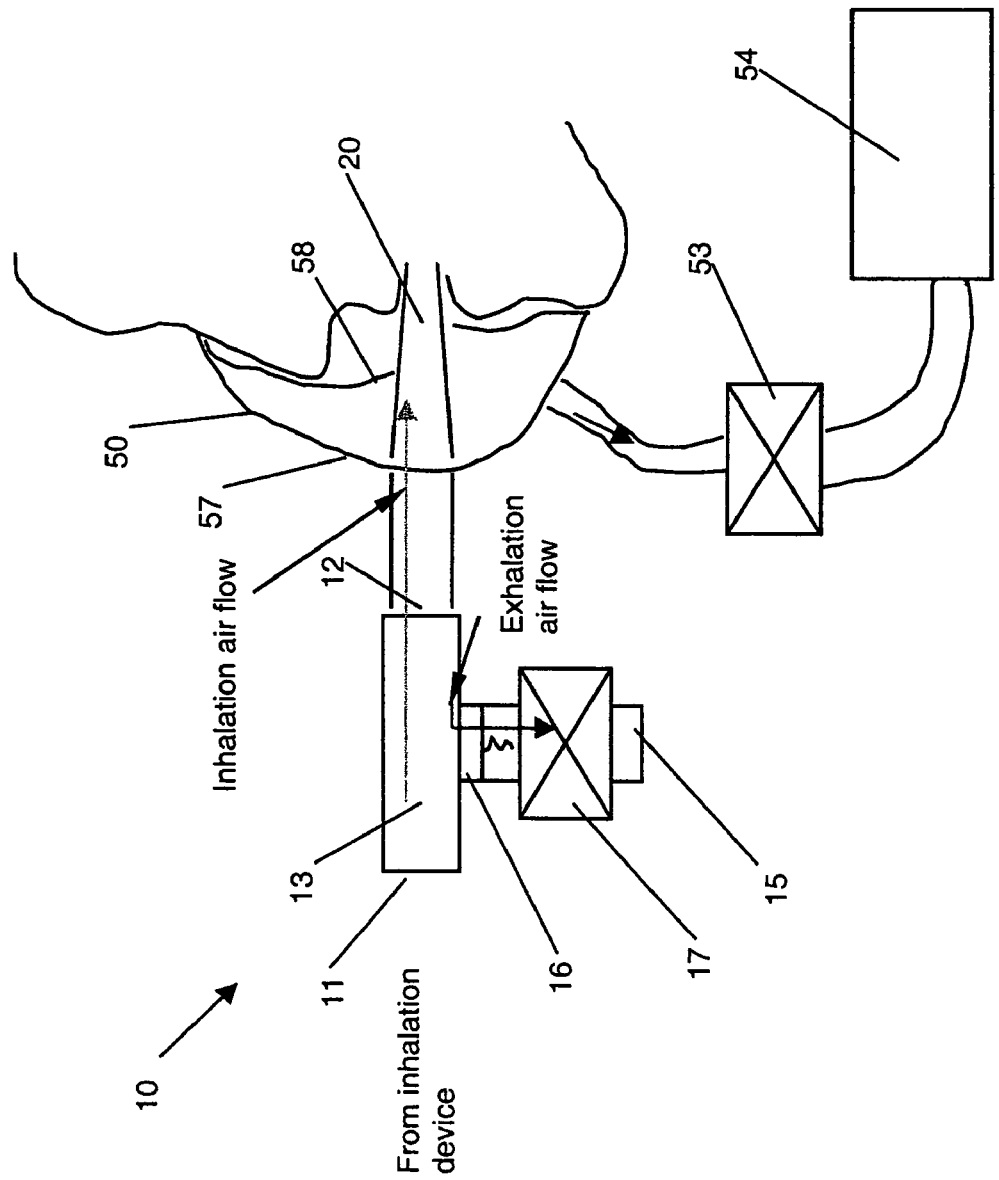
FIG. 9 illustrates a component according to a fifth embodiment of the invention.

FIG. 5 illustrates the basic structure of an inhalation device 1 of the invention for the inhalation of toxic pharmaceuticals. The inhalation device comprises an inhalation apparatus 2 which contains the control electronics, enter keys, display, etc. and is connected to a nebulizer 30 via a corresponding connecting cable 3 for air, data and current. The active ingredient to be applied is nebulized in the nebulizer 30 and fed into a compressed air flow, which is connected to a mask 50 via a corresponding tube 18, the component 10 according to the invention and a further tube 18 (or a mouthpiece (not shown)). The mask 50 is attached to patient's face thereby covering his/her mouth and nose. The component 10 according to the invention comprises a filter 17, which, upon inhalation of toxic agents, filters the residues of the toxic agents present in the exhaled air out of the exhaled air and thus purifies the exhaled air. Accordingly, FIG. 5 illustrates a preferred further filter 53, which is directly connected to the interior of the inhalation mask 50 via a corresponding tube. A suction device 54, which is also controlled by the inhalation device 2 via a connecting tube 4 illustrated in phantom, sucks the exhaled air off the inhalation mask 50 via the filter 53.

According to FIG. 6*a,* the component 10 according to the invention comprises a first flow channel 13 between a first air inlet opening 11 and a first air outlet opening 12. The inhalation of the nebulizer takes place via the first flow channel 13 and via the mouthpiece 20. To this end, the patient puts the end of the mouthpiece, i.e., the mouthpiece tip 21, into the mouth, as shown in FIG. 6*b.* A second flow channel 16 is provided for exhalation which extends between a second air inlet opening 14 and a second air outlet opening 15. In the embodiment shown in FIGS. 6*a* and 6*b,* the first air outlet opening 12 and the second air inlet opening 14 coincide. In this embodiment, the component 10 of the invention is formed as a three-way valve, which allows an inhalation via the first flow channel 13, however, an exhalation only via the second flow channel 16. In the second flow channel 16, a filter 17 is provided, which purifies and decontaminates the exhaled air. According to the embodiment of FIGS. 6*a*/6*b,* a suction device 40 is connected to the second flow channel 16 via a tube 41 to suck out the exhaled air.

In the embodiment according to FIG. 6*a,* a protection element 22 is further provided, which is preferably self-expandable, e.g., bellows. The protection element 22 is expanded in its idle state, as shown in FIG. 6*a,* but is compressible when the inhalation device is used, as shown in FIG. 6*b* so that the patient can put the mouthpiece into the mouth. In its expanded state, the protection element 22 extends beyond the tip 21 of the mouthpiece 20. Thus, when the user removes the component of the inhalation device from the mouth, the protection element 22 expands automatically to thus provide its protective function: contaminated air is kept in the protection element 22 and cannot escape into the environment, but is sucked out and filtered. In order to enable the user to exhale or exhale more easily before the inhalation process starts or during a break, the protection element 22 preferably has an exhalation valve 23. Thus, the patient can exhale also when the bellows are attached to his/her face as illustrated in FIG. 6*b.*

An alternative embodiment of the component of the invention is illustrated in FIG. 7. In contrast to the component of FIG. 2, no mouthpiece 20 is provided which the patient puts into the mouth. Rather, the inhalation air flow ends in an inhalation mask 50 which is dimensioned such that it covers the mouth and nose of the patient. A "mouthpiece", i.e., a tube connection extends from the first air outlet opening 12 to an opening 51 in the inhalation mask 50. Further, a second opening 52 is provided in the inhalation mask 50, the opening connecting the interior of the inhalation mask 56 to a suction device 54 via a filter 53. Exhaled air can be sucked out via this channel. Moreover, exhaled air is removed via the component 10 of the invention and in particular via the second flow channel 16 and the filter 17.

FIG. 8 illustrates an embodiment similar to the embodiment of FIG. 7. In the embodiment of FIG. 8, a mouthpiece 20 is additionally provided. The mouthpiece 20 facilitates inhalation of the patient since he/she may put its tip 21 into the mouth and inhale comfortably only via the flow channel. In this embodiment, the exhalation takes place, e.g., through the nose so that the patient can keep the mouthpiece in the mouth. Such exhaled air is sucked out directly from the interior 56 of the mask via the filter 53 by the suction device 54. However, in order to prevent that the mask 50 is put over the patient's face in case of a negative pressure in the interior 56 of the mask, the inhalation mask 50 is designed in the circumferential area 55 such that an air inlet is possible. As explained above, one-way valves are provided as an alternative ensuring a necessary pressure compensation. Thus, e.g., as soon as there is a negative pressure in the interior 56 of the mask via the suction device 54, ambient air may flow in via the circumferential or peripheral area 55 or a one-way valve (not shown). The same is true for the embodiment shown in FIG. 7.

If, in the embodiment of FIG. 8, exhalation is performed not only through the nose but also or exclusively through the mouth, the exhaled air is removed and purified via the second flow channel 16 and the filter 17.

FIG. 9 illustrates a further embodiment of the component 10 of the invention. According to this embodiment, a particularly preferred inhalation mask 50 is used, which is shown in more detail in FIG. 12. This inhalation mask 50 is designed in the form of a balloon and is penetrated in a first portion 57 by the mouthpiece 20. This first portion 57 is the portion of the inhalation mask 50 which is turned away from the patient's face during inhalation. The opposing portion 58, however, is turned towards the patient's face during inhalation. Prior to the inhalation, the portion 58 extends beyond the mouthpiece tip 21, as shown in FIG. 11. This is also a protective function as explained above in connection with FIG. 6. Possibly contaminated air which is escaping is kept in the mask 50 and sucked out. However, as soon as the patient pulls over the inhalation mask and presses it against the face, the tip, i.e., the end 21 of the mouthpiece 20 extends beyond the portion 58 of the inhalation mask so that the patient can put the mouthpiece into the mouth. The portion 58 is only put over the mouthpiece 20 as illustrated in FIG. 9.

FIG. 9 illustrates the inhalation mask according to the invention when already put on. In other respects, this embodiment is identical to the one shown in FIG. 8 so that reference is made to the explanations concerning FIG. 8.

FIGS. 10 and 11 illustrate an alternative of the design of the inhalation mask 50 and mouthpiece 20. According to this alternative embodiment, the mouthpiece 20 is flexibly positioned and movably attached with regard to the inhalation mask 50. FIG. 10 shows the mouthpiece vis-á-vis the inhalation mask in a position where the patient inhales. In order to facilitate the exhalation, the mouthpiece can be withdrawn, i.e., removed from the patient, as shown in FIG. 11. To this end, the patient releases the mouthpiece end 21 and it is withdrawn sufficiently far into the interior 56 of the mask so that the patient can comfortably exhale. The exhaled air is then sucked out, e.g., via the suction device 54. As shown in FIGS. 10 and 11, bellows 59 or another flexible element is provided in order to flexibly and movably position the mouthpiece 20. If the patient pushes the mouthpiece 20 into the mouth, as shown in FIG. 10, said flexible element is 59 is compressed. In case of a self-expandable flexible element 59, the mouthpiece 20 retracts automatically when released by the patient.

Figure 10:
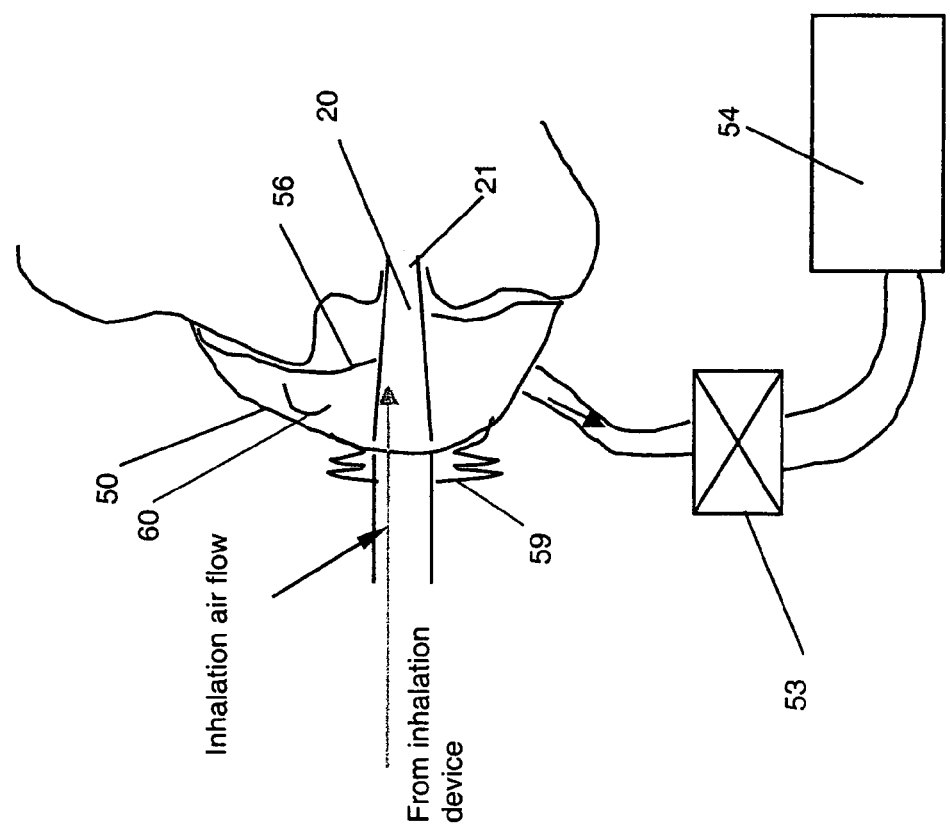
FIG. 10 illustrates the use of a preferred inhalation mask during inhalation.
Figure 11:
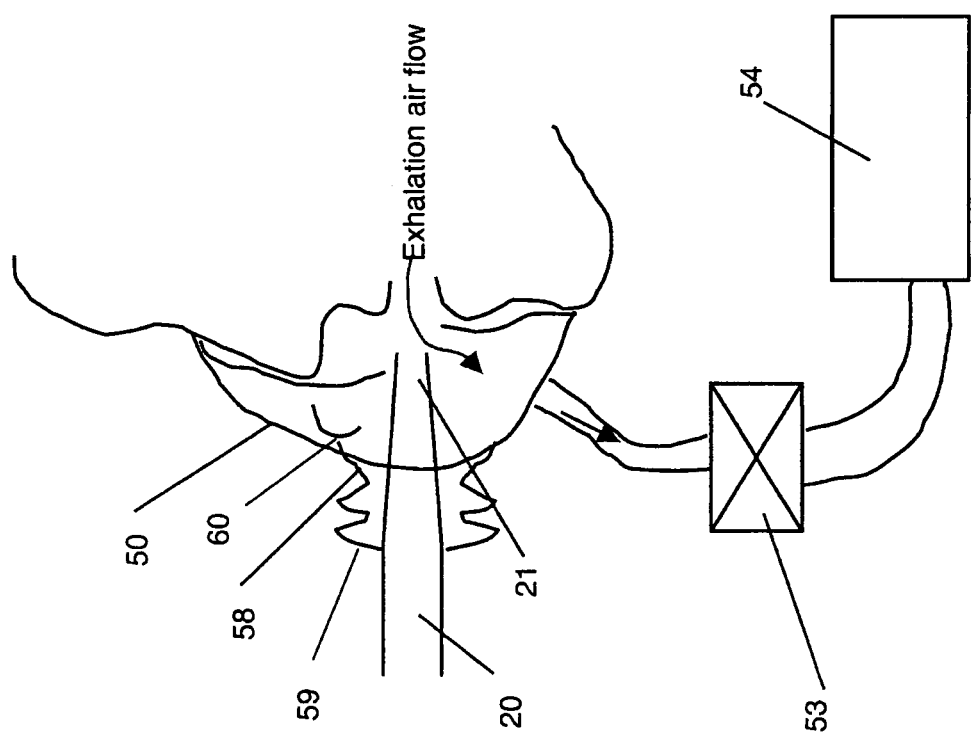
FIG. 11 illustrates the use of a preferred inhalation mask during exhalation.

The embodiments of FIGS. 10 and 11 also show the one-way valve 60 of the mask 50 for pressure compensation.

A further alternative is illustrated in FIG. 13. This corresponds basically to the embodiment of FIG. 10. In FIG. 13, however, a buffer element 61 is additionally shown, which serves as exhalation buffer, i.e., exhalation bag. If the suction rate is too low, it is thus ensured that the patient can still exhale normally. Exhaled air which is not sucked out is then buffered in the exhalation buffer and sucked out with delay while the patient inhales again. Such a buffer can be provided in all embodiments.

In the embodiment of FIG. 14 a pressure sensor 62 is further provided. This pressure sensor measures the pressure in the interior 56 of the mask and supplies the suction device 54 with the result. The suction device 54 may then set a suction rate depending on or controlled according to the pressure.

According to the present invention, various embodiments of an inhalation device component and an inhalation device comprising these components are possible. Some of these alternative embodiments are listed below. Reference numerals for the features of the inhalation device components described above are included in the various listed embodiments.

1. A component for an inhalation device (1) comprising:
   a first flow channel (13) for inhalation;
   a second flow channel (16) for exhalation;
   a mouthpiece (20) forming a part of the first flow channel (13);
   a filter (53) assigned to the second flow channel (16); and
   a protection element (59) circumferentially surrounding the mouthpiece (20); characterised in that
   the protection element (59) is sealingly connected to the mouthpiece (20) at the end opposing the tip (21) of the mouthpiece.

2. The component according to embodiment 1, further comprising an inhalation mask (50) connected to the end of the protection element (59) opposing the junction (66) of the mouthpiece (20) and protection element (59).

3. The component according to embodiments 1 or 2, wherein the flow channel (16, 65) for exhalation begins at the junction (66) of the mouthpiece (20) and protection element (59).

4. The component according to embodiment 2, wherein the flow channel (16, 65') for exhalation begins at the inhalation mask (50).

5. The component according to one of the preceding embodiments, wherein the second flow channel (16, 65, 65') is connectable to a suction device (54).

6. The component according to one of the preceding embodiments, wherein the second flow channel (16, 65, 65') for exhalation has an expiration valve (64).

7. The component according to embodiment 6, wherein the expiration valve (64) is arranged downstream from the filter (53).

8. The component according to one of the preceding embodiments, wherein the wall of the mouthpiece (20) has an expiration valve (24).

9. The component according to one of the preceding embodiments, wherein the first flow channel (13) for inhalation is connectable to a nebulizer (30).

10. The component according to one of embodiments 1 to 9, wherein the excess length of the protection element (59) vis-á-vis the tip (21) of the mouthpiece is between 5 and 100 mm.

11. The component according to one of embodiments 1 to 10, wherein the protection element (59) is self-expandable.

12. The component according to one of embodiments 1 to 11, wherein the protection element (59) is formed as bellows.

13. The component for an inhalation device (1) comprising:
    a first air inlet opening (11) and a first air outlet opening (12), which are connected via a first flow channel (13) for the inhalation;
    a second air inlet opening (14) and a second air outlet opening (15), which are connected via a second flow channel (16) for exhalation;
    a first filter (17) assigned to the second flow channel;
    an inhalation mask (50) in which the first flow channel (13) ends and at which the second flow channel (16) starts;
    characterised in that the inhalation mask (50) has a third air inlet opening in the form of a valve (63) for a third flow channel in order to ensure a continuous air flow;
    wherein the exhalation takes place via the second flow channel (16).

14. The component according to embodiment 13, wherein upon termination of the inhalation, the first flow channel (13) is closed and the second flow channel (16) is opened.

15. The component according to embodiment 13 or 14, wherein the first air outlet opening (12) and the second air inlet opening (14) coincide.

16. The component according to one of embodiments 13 to 15, wherein the first flow channel (13) and the second flow channel (16) form a three-way valve.

17. The component according to one of embodiments 13 to 17, wherein the first air outlet opening (12) and the second air inlet opening (14) are connectable to a mouthpiece (20).

18. The component according to embodiment 17, further comprising a protection element (22) circumferentially surrounding the mouthpiece (20) and extending beyond the tip (21) of the mouthpiece.

19. The component according to embodiment 18, wherein the protection element (22) is sealingly connected to the mouthpiece (20) at the end opposing the mouthpiece tip (21).

20. The component according to one of embodiments 18 or 19, wherein the excess length of the protection element (22) vis-á-vis the mouthpiece tip (21) is between 5 and 100 mm.

21. The component according to one of embodiments 18, 19 or 20, wherein the protection element (22) is self-expandable.

22. The component according to one of embodiments 18 to 21, wherein the protection element (22) is formed as bellows.

23. The component according to one of embodiments 17 to 22, wherein the inhalation mask (50) has a first opening (51) at which the first flow channel (13) ends.

24. The component according to embodiment 23, wherein the mouthpiece (20) penetrates the inhalation mask (50) and extends into the interior (56) of the mask formed by the inhalation mask (50) and the face of the user.

25. The component according to embodiment 23 or 24, wherein the mouthpiece (20) is arranged movably between an inhalation position, where the user can put the mouthpiece (20) into the mouth, and an exhalation position, where the mouthpiece (20) is withdrawn in the interior (56) of the mask, in the first opening (51).

26. The component according to one of embodiments 2 to 25, wherein the inhalation mask (50) is formed in the circumferential area (55) such that a pressure compensation via the circumferential area (55) is possible if there is a negative pressure in the interior (56) of the mask formed by the inhalation mask (50) and the face of the user.

27. The component according to one of embodiments 2 to 26, wherein the inhalation mask (50) has at least a one-way valve (60) for pressure compensation in the interior (56) of the mask.

28. The component according to one of embodiments 2 to 27, wherein the inhalation mask (50) is designed in the form of a balloon.

29. The component according to embodiment 28, wherein the mouthpiece (20) penetrates the inhalation mask (50) in a first portion (57) turned away from the user's face and extends into the interior (56) of the mask and an opposing second portion (58) turned towards the face of the user can be penetrated by the mouthpiece tip (21) when the inhalation mask (50) is put on.

30. The component according to one of embodiments 13 to 29, wherein the second air outlet opening (15) is connectable to a suction device (40).

31. The component according to one of embodiments 13 to 30, wherein the first air inlet opening (11) is connectable to a nebulizer (30).

32. The component according to one of embodiments 1 to 31, wherein the component is part of the aerosol generator of the inhalation device.

33. An inhalation device comprising a first flow channel for the inhalation and a second flow channel for the exhalation, wherein means are provided which prevent that prior to, during and after the inhalation by the user active ingredients emitted by the inhalation device escape into the environment.

34. The inhalation device according to embodiment 33, wherein the inhibition means comprise a component according to one of claims 1 to 12, further comprising a nebulizer (30) connected to the first flow channel.

35. The inhalation device according to embodiment 34, further comprising a suction device connected to the second flow channel.

36. The inhalation device according to embodiment 35, wherein the inhalation mask (50) further comprises a pressure sensor (62), which is operationally connected to the suction device and/or the inhalation device.

The invention is further set forth in the claims listed below. This invention may take on various modifications and alterations without departing from the spirit and scope thereof. In describing embodiments of the invention, specific terminology is used for the sake of clarity. The invention, however, is not intended to be limited to the specific terms so selected, and it is to be understood that each term so selected includes all technical equivalents that operate similarly.

The invention claimed is:

1. A component for an inhalation device comprising:
    a first air inlet opening and a first air outlet opening, which are connected via a first flow channel for inhalation;
    a second air inlet opening and a second air outlet opening, which are connected via a second flow channel for exhalation;
    a first filter assigned to the second flow channel;
    an inhalation mask at which the first flow channel ends and at which the second flow channel begins; wherein the inhalation mask has a third air inlet opening in the form of a valve for a third flow channel in order to ensure a continuous air flow; and wherein the exhalation takes place via the second flow channel.

2. The component according to claim 1, wherein the first air outlet opening and the second air inlet opening are connectable to a mouthpiece having a tip.

3. The component according to claim 2, further comprising a protection element circumferentially surrounding the mouthpiece and extending beyond the tip of the mouthpiece.

4. The component according to claim 3, wherein the protection element is sealingly connected to the mouthpiece at the end opposing the mouthpiece tip.

5. The component according to claim 2, wherein the mouthpiece penetrates the inhalation mask and extends into an interior space of the mask formed by the inhalation mask.

6. The component according to claim 2, wherein the mouthpiece is arranged movably between an inhalation position, where a user can put the mouthpiece into a mouth, and an exhalation position, where the mouthpiece is withdrawn into an interior space of the mask.

7. The component according to claim 1, wherein the inhalation mask is formed in a circumferential area such that a pressure compensation via the circumferential area is possible if there is a negative pressure in an interior space of the mask formed by the inhalation mask and a face of a user.

8. The component according to claim 1, wherein the inhalation mask has at least a one-way valve for pressure compensation in an interior space of the mask.

9. The component according to claim 1, wherein the inhalation mask is designed in a form of a balloon.

10. An inhalation device comprising a component for an inhalation device comprising: a first air inlet opening and a first air outlet opening, which are connected via a first flow channel for inhalation; a second air inlet opening and a second air outlet opening, which are connected via a second flow channel for exhalation; a first filter assigned to the second flow channel; an inhalation mask at which the first flow channel ends and at which the second flow channel begins; wherein the inhalation mask has a third air inlet opening in the form of a valve for a third flow channel in order to ensure a continuous air flow; and wherein the exhalation takes place via the second flow channel, wherein means are provided to prevent escape of active ingredients emitted by the inhalation device into the environment before, during and after inhalation by a user.

11. The inhalation device according to claim 10, wherein the inhalation device comprises an aerosol generator.

12. The inhalation device according to claim 10, further comprising a nebulizer connected to the first flow channel.

13. The inhalation device according to claim 10, further comprising a suction device connected to the second flow channel.

14. The component according to claim 1, wherein upon termination of inhalation, the first flow channel is closed and the second flow channel is opened.

15. The component according to claim 1, wherein the first air outlet opening and the second air inlet opening coincide.

16. The component according to claim 1, wherein the first flow channel and the second flow channel form a three-way valve.

17. The component according to claim 3, wherein an excess length of the protection element vis-à-vis the mouthpiece tip is between 5 and 100 mm.

18. The component according to claim 3, wherein the protection element is self-expandable.

19. The component according to claim 3, wherein the protection element is formed as a bellows.

20. The component according to claim 1, wherein a mouthpiece having a tip penetrates the inhalation mask in a first portion turned away from a user's face and extends into an interior space of the mask and an opposing second portion turned towards the face of the user can be penetrated by inhalation mouthpiece tip when the inhalation mask is put on.

21. The component according to claim 1, wherein the component is part of an aerosol generator of an inhalation device.

22. The inhalation device according to claim 13, further comprising a pressure sensor, which is operationally connected to a suction device or to the inhalation device or to both.

* * * * *

UNITED STATES PATENT AND TRADEMARK OFFICE
CERTIFICATE OF CORRECTION

PATENT NO. : 7,647,928 B2 Page 1 of 1
APPLICATION NO. : 11/358263
DATED : January 19, 2010
INVENTOR(S) : Muellinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this

Sixteenth Day of November, 2010

David J. Kappos
*Director of the United States Patent and Trademark Office*